United States Patent
Janssen

(10) Patent No.: US 7,032,251 B2
(45) Date of Patent: Apr. 25, 2006

(54) CROSSLINKING AGENT FOR COATED ELASTOMERIC ARTICLES

(75) Inventor: Robert A. Janssen, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 208 days.

(21) Appl. No.: 10/316,149

(22) Filed: Dec. 10, 2002

(65) Prior Publication Data

US 2004/0107477 A1 Jun. 10, 2004

(51) Int. Cl.
*A41D 19/00* (2006.01)

(52) U.S. Cl. .................................................. 2/161.6
(58) Field of Classification Search ................ 2/161.7, 2/168, 167, 169; 428/383
See application file for complete search history.

(56) References Cited

U.S. PATENT DOCUMENTS

| | | | |
|---|---|---|---|
| 3,224,986 A | 12/1965 | Butler et al. | |
| 3,566,874 A | 3/1971 | Shepherd et al. | |
| 3,813,695 A | 6/1974 | Podell, Jr. et al. | |
| 3,861,396 A | 1/1975 | Vaillancourt et al. | |
| 3,895,166 A * | 7/1975 | Wood | 428/383 |
| 4,132,695 A | 1/1979 | Burkholder | |
| 4,154,898 A | 5/1979 | Burkholder, Jr. | |
| 4,499,154 A | 2/1985 | James et al. | |
| 4,527,293 A | 7/1985 | Eckstein et al. | |
| 4,548,844 A | 10/1985 | Podell et al. | |
| 4,575,476 A | 3/1986 | Podell et al. | |
| 5,061,738 A * | 10/1991 | Solomon et al. | 523/100 |
| 5,112,900 A | 5/1992 | Buddenhagen et al. | |
| 5,407,715 A | 4/1995 | Buddenhagen et al. | |
| 5,688,855 A | 11/1997 | Stoy et al. | |
| 5,792,531 A | 8/1998 | Littleton et al. | |
| 5,804,318 A | 9/1998 | Pinchuk et al. | |
| 6,007,526 A * | 12/1999 | Passalaqua et al. | 604/349 |
| 6,106,889 A * | 8/2000 | Beavers et al. | 427/2.1 |
| 6,221,061 B1 * | 4/2001 | Engelson et al. | 604/265 |
| 6,306,514 B1 | 10/2001 | Weikel et al. | |
| 6,340,465 B1 * | 1/2002 | Hsu et al. | 424/400 |
| 6,479,227 B1 * | 11/2002 | Kubo et al. | 430/523 |
| 6,482,221 B1 * | 11/2002 | Hebert et al. | 606/194 |
| 6,551,267 B1 * | 4/2003 | Cohen et al. | 604/6.15 |

FOREIGN PATENT DOCUMENTS

| | | |
|---|---|---|
| EP | 0455323 A2 | 11/1991 |
| WO | WO 9821270 A1 | 5/1998 |

OTHER PUBLICATIONS

Product Data Sheet for Kymene® 557LX Wet–Strength Resin by Hercules, Inc., 2 pages.
PCT Search Report, Jan. 8, 2004.

* cited by examiner

*Primary Examiner*—Katherine M Moran
(74) *Attorney, Agent, or Firm*—Dority & Manning, P.A.

(57) ABSTRACT

Disclosed is an elastomeric article, such as a glove, and a process for making the elastomeric articles. The elastomeric articles include a primary matrix including one or more layers of elastomeric polymer, such as a natural or synthetic latex or a block copolymer, and a polymeric coating on a surface of the primary matrix. The polymeric coating is formed of crosslinked polymers which are crosslinked with a cationic crosslinking agent such as a polyamide epichlorohydrin crosslinking agent. The polymeric coating can be a crosslinked polyarcylate, polyacrylamide, or polysaccharise, for example. In one embodiment, the crosslinking agent crosslinks the polymeric coating to the primary matrix layer of the article, forming secure attachments between the primary matrix and the polymeric coating. In one embodiment, the crosslinking agent may crosslink the elastomeric polymer as well as the polymeric coating. In one embodiment, the polymeric coating is a donning coat on a glove and may include a suitable lubricant applied to the surface of the donning coat.

38 Claims, 4 Drawing Sheets

CROSSLINKING AGENT FOR COATED ELASTOMERIC ARTICLES

BACKGROUND OF THE INVENTION

Elastomeric materials have been formed into countless different articles suitable for use in many applications, such as surgical gloves, examining gloves, condoms, catheters, balloons, tubing, and the like. Elastomeric materials have been found particularly suitable for such applications due to their physical characteristics. For example, elastomeric materials, in addition to having good elastic properties, exhibit good strength characteristics and may be produced so as to be impermeable not only to aqueous solutions, but also to many solvents and oils.

Elastomeric materials are typically tacky to the touch and present a somewhat sticky surface. Tackiness of the surface of the article often renders manufacture and use of the article difficult, at best. For example articles such as gloves, catheters, or balloons may stick to formers during manufacture and to themselves and each other during packaging and shipping. In addition, elastomeric articles often feel sticky to human skin. For example, elastomeric articles such as gloves may be difficult to slip over the hand during donning due to tackiness at the glove surface. Historically, the most common process for decreasing surface tackiness of an elastomeric article has been the addition of a powder to the article's surface. The powder acts as a buffer or barrier between the surface of the article and other materials to make the elastomeric article feel more slippery. While powder on the article surface is acceptable for some applications, powders may not be desired in certain applications, such as surgical or other clean-room type applications.

As a result, powder free coatings have been developed for elastomeric articles in an attempt to provide the articles with increased slip at the surface. For instance, hydrophilic coatings such as hydrophilic hydrogel polymer systems have been used to form coatings on elastomeric materials in an attempt to decrease surface friction. In order to form the thin coatings on the elastomeric articles, such polymer systems have often been cured in the presence of a formaldehyde based crosslinking agent and a catalyst, such as a paratoluene sulfonic acid catalyst.

Problems have been encountered with these systems, however. For instance, highly hydrophilic coatings absorb a great deal of water, causing substantial volume changes in the coating during hydration and drying. This may lead to delamination and peeling of the coating from the glove surface. Additionally, highly hydrophilic polymers are often quite rigid in the dry state. This may lead to cracks forming in the coating, which may also lead to delamination of the coating from the surface of the elastomeric article.

In addition, the chemicals used in forming the coatings, for example, the formaldehyde-based cross linking agents and toluene-based catalysts, may present waste disposal problems due to their toxicity.

As such, a need currently exists for an elastomeric article with a suitable surface coating which may provide the desired surface characteristics as well as avoid peeling or delamination of the coating from the article surface. Moreover, a need exists for an elastomeric article which does not incur waste disposal problems due to the presence of formaldehyde-based cross-linking agents.

SUMMARY OF THE INVENTION

The present invention is directed to an elastomeric article and a method for producing the elastomeric article. In one embodiment, the elastomeric article may be an elastomeric glove.

The elastomeric article of the present invention includes a base layer of a suitable elastomeric polymer and a polymeric coating on a surface of the base layer. The polymeric coating of the present invention is crosslinked with a polyamide epichlorohydrin crosslinking agent. In one embodiment, the polymer forming the polymeric coating may include crosslinked polyacrylates, polyacrylamides, or polysaccharides.

The process of the present invention, in one embodiment, includes contacting a former with an elastomeric material to form a primary matrix according to the shape of the former. After the primary matrix of the elastomeric article has been formed, the former is contacted with a solution containing a polymer for forming a polymeric coating on the primary matrix. After removing excess moisture, the polymer forming the coating may be crosslinked with a polyamide epichlorohydrin crosslinking agent. The crosslinking agent may optionally be in solution with the polymer, with the elastomeric material, or in a separate contact solution, as desired.

BRIEF DESCRIPTION OF THE DRAWINGS

A full and enabling disclosure of the present invention, including the best mode thereof to one of ordinary skill in the art, is set forth more particularly in the remainder of the specification, including reference to the accompanying figures in which.

DETAILED DESCRIPTION OF PREFERRED EMBODIMENTS

It is to be understood by one of ordinary skill in the art that the present discussion is a description of exemplary embodiments only, and is not intended as limiting the broader aspects of the present invention, which broader aspects are embodied in the exemplary construction. Moreover, it should be further understood, that even though the elastomeric articles referred to in the remainder of this description are generally referred to as gloves, the present invention is applicable to other elastomeric articles as well, and is not to be limited to gloves.

Figure 2:
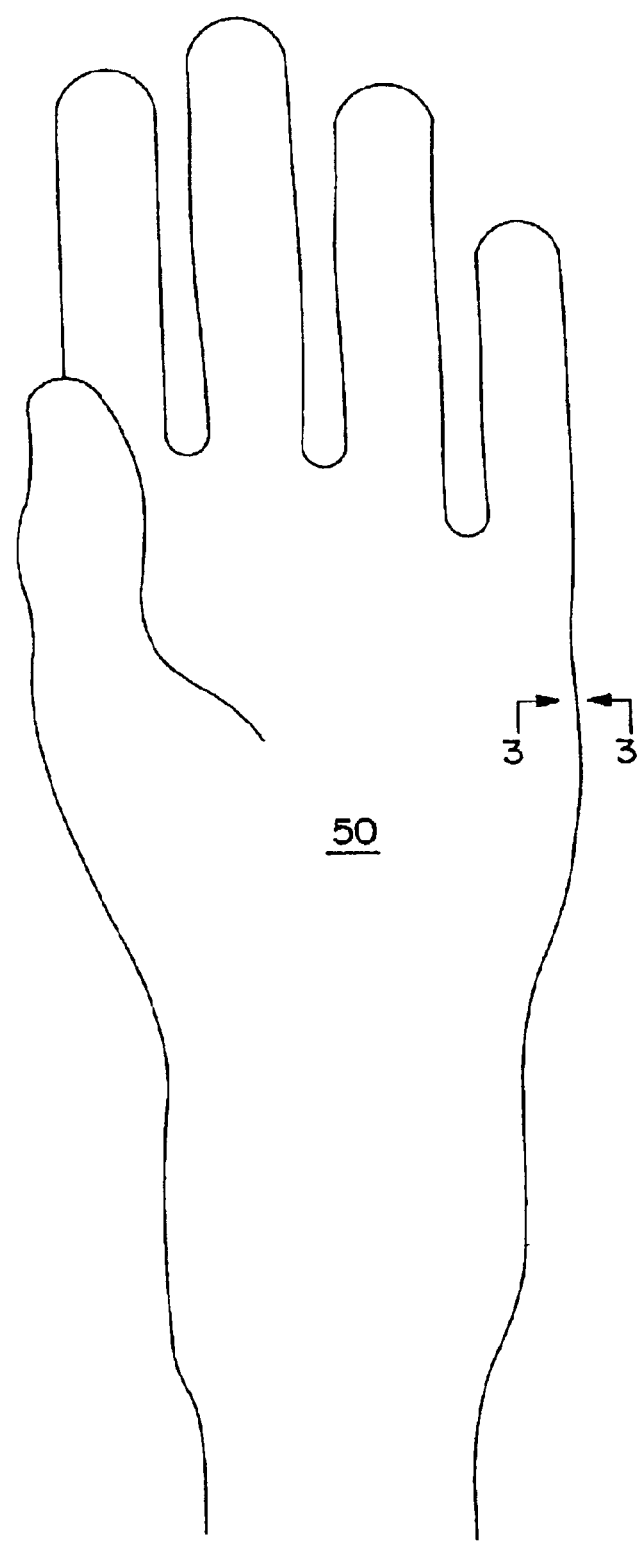
FIG. 2 is a front view of a glove according to the present invention.
Figure 4:
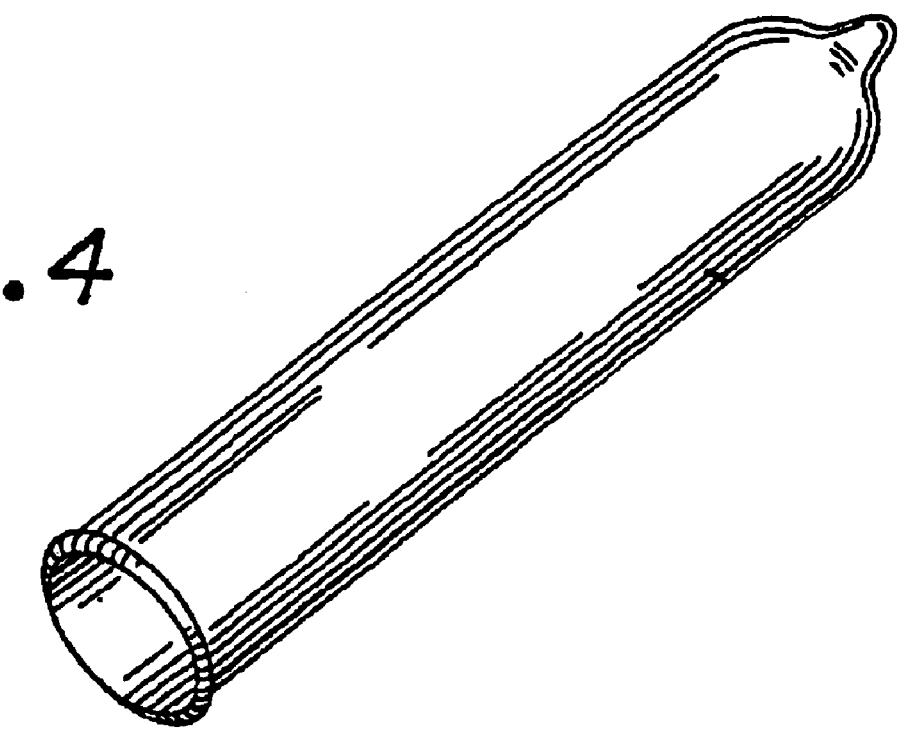
FIG. 4 is a perspective view of a condom according to the present invention.

The present invention is generally directed to a crosslinked polymer coating applied to a surface of an elastomeric article, such as a glove as shown in FIG. 2 or a condom as shown in FIG. 4. In one embodiment, the polymer coating may be formed on the skin contacting surface of a glove as a donning layer. The polymer coating may optionally be formed directly on a former prior to formation of the primary matrix of a glove as a release coat or a gripping layer. The polymers which may be used to form the polymeric coating of the present invention contain negatively charged functional groups or linkages such as, for instance, ester linkages to hydroxyl groups or amine groups, carboxylic acid groups, ether linkages or the like. The negatively charged component on the polymer provides reactive sights for reaction between the polymer and a cationic crosslinking agent. For example, the polymers may be crosslinked with a cationic polyamide epichlorohydrin (PAE) crosslinking agent.

The cationic crosslinking agent may provide numerous benefits to the gloves of the present invention. For example, in certain embodiments, in addition to reacting with the polymer to form a crosslinked polymeric coating, the cationic crosslinking agent may also react with negatively charged components of the elastomeric material forming the primary matrix of the glove. For instance, when a natural rubber latex glove is formed, a cationic crosslinking agent such as a PAE crosslinking agent may react with negatively charged components on the elastomeric material as well as read with the coating polymer chains and form crosslinks between the polymeric coating on the glove surface and the elastomeric polymer. Thus, a secure attachment is formed between the polymeric coating and the primary matrix of the glove. Additionally, in some embodiments, a PAE crosslinking agent can be used to crosslink the elastomeric polymer forming the primary matrix of the glove in order to cure or vulcanize the rubber.

In addition, a cationic crosslinking agent such as PAE will not cause the waste disposal problems that formaldehyde-based crosslinking agents used in the past may cause. The addition of formaldehydes to the waste stream may lead to increase of pollutants such as formaldehyde-based ground water pollutants and is therefore to be avoided wherever possible.

Any elastomeric article may be processed according to the present invention. For example, the gloves of the present invention may be formed of a natural or a synthetic latex or a dissolved elastomeric polymer, as desired. For instance, the gloves of the present invention may be formed of a natural rubber, a nitrile rubber, a polyurethane, a homopolymer of a conjugated diene, a copolymer of a least two conjugated dienes, a copolymer of at least one conjugated diene and at least one vinyl monomer, or any other suitable combinations thereof. For example, the glove may be a polyvinyl chloride glove, as is known in the art. Moreover, combinations of polymers or copolymers may be in a single layer of an article or in separate layers, such as in a multi-layer article.

Figure 1:
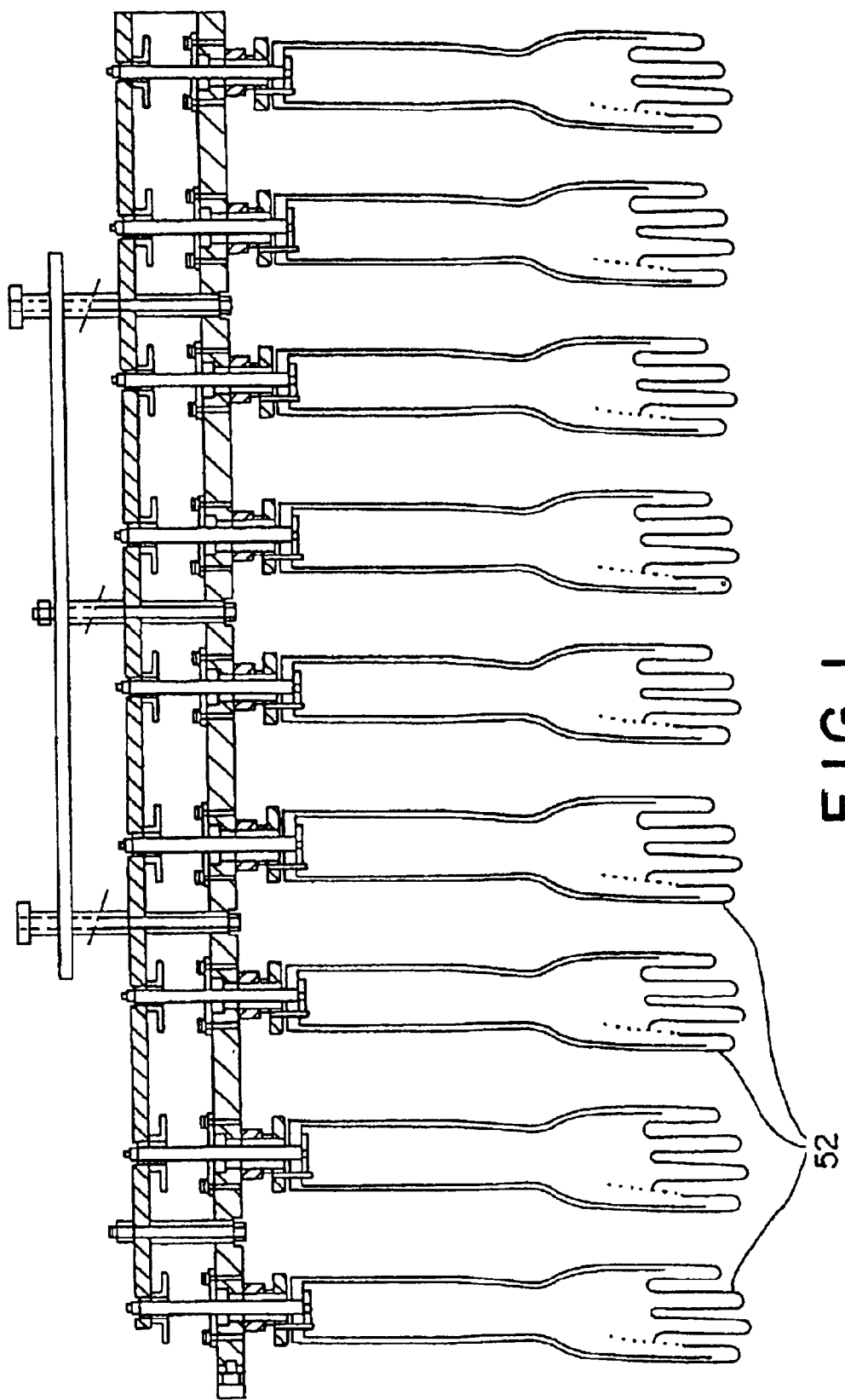
FIG. 1 is an illustration of glove-shaped formers that may be used in accordance with one embodiment of the present invention.

In general, the elastomeric articles of the present invention may be formed by any suitable process. For example, an elastomeric glove may be formed by a series of dipping processes of a former of the shape of the finished article. FIG. 1 is an illustration of a series of glove molds or formers 52 which may be used to form the gloves of the present invention. The formers 52 shown in FIG. 1 are illustrated on a pallet as is conventionally used in a batch processing operation, but it should be understood that the process of the present invention may equally be utilized in a continuous operation. A former 52 may generally be a contoured mold having a textured or smooth surface which may accept a series of coatings and release the formed article. Possible materials for the surface of former 52 may include any suitable surface material. For example, the surface of former 52 may be formed of ceramic, porcelain, glass, metal, or certain fluorocarbons.

If desired, a former may be cleaned prior to formation of a glove on the former. The cleaning process may generally include an optional water pre-rinse followed by an acid wash. After the acid wash, the former may be rinsed with water and dipped in a heated caustic solution prior to a final water rinse. After the cleaning process, a glove may be formed on the former through a series of dipping and drying steps.

FIG. 2 illustrates one possible embodiment of a glove 50 which may be formed on former 52. In one embodiment, the glove 50 may be formed through a series of dippings or immersions of the former 52. For example, a former release coating can be formed on the former prior to formation of the main body of the elastomeric article. A former release coating may prevent excessive adhesion between the former and the glove, improving the stripping ability of the glove. In one embodiment, a polymeric former release coating may be formed according to the processes of the present invention prior to formation of any other coatings on the former. A former release coating may optionally include other additives, such as a coagulant composition, for instance.

In one embodiment, after cleaning and the formation of a former release coating, when desired, the former 52 may be dipped into a coagulant composition prior to forming the main body or primary matrix of the glove on the former. For purposes of this disclosure, the primary matrix of the glove is defined to be the main body of the glove and includes one or more layers of elastomeric material. A coagulant causes a base latex polymer which may form the primary matrix of the glove to coagulate. Coagulants that may be used in the present invention may include powders, to ease stripping of the glove from the former, or, if desired, may be powder free coagulant compositions. In one embodiment, a powder free coagulant composition may be used which includes water soluble salts of calcium, zinc, aluminum, and the like. For example, in one embodiment, calcium nitrate in water or alcohol may be used in the coagulant composition. In such an embodiment, calcium nitrate may be present in the solution in an amount of up to about 40% by weight. Optionally, the coagulant composition may also contain additives such as surfactants.

After being immersed in the coagulant composition, the former is withdrawn and the coagulant present on the surface of the former is permitted to dry. For many applications, the coagulant may be air dried for a time of from about one minute to about two minutes. Once dried, a residual coating of the coagulant is left on the former.

If desired, the coagulant composition may contain certain additives. For example, the coagulant composition may contain various additives which may improve the tactile or other characteristics of a surface of the glove.

In one embodiment, after the coagulant dip, the former may be immersed or dipped into a latex emulsion of the desired elastomeric polymer. A latex is defined for the purposes of this invention as a colloid in which the elastomeric polymer is suspended in water.

In general, a latex emulsion of the present invention may have a dry rubber content (DRC) of less than about 50% or alternatively a total solid content (TSC) of less than about 50%. In one embodiment, a latex emulsion may have a DRC or a TSC content of less than about 25%. A latex emulsion may also contain various additives such as pH adjustors, stabilizers, and the like as are generally known in the art.

Upon contact of the latex with the coagulant composition, the coagulant may cause some of the latex to become locally unstable and coagulate on the surface of the former. Any additives in the coagulant composition may, depending upon what they are, form a layer between the former and the latex film such as a former release layer, for example, or alternatively may be incorporated into the latex film and may subsequently be removed during a leaching process. After the desired amount of time, the former is withdrawn from the latex emulsion, and the coagulated layer is allowed to coalesce fully on the former.

The amount of time the former is immersed in the emulsion (commonly termed "dwell time") determines the thickness of the film. Increasing the dwell time of the former in the latex causes the thickness of the film to increase. The total thickness of the film forming the glove body may depend on other parameters as well, including, for example, the solids content of the latex emulsion and the additive content of the latex emulsion and/or the coagulant composition.

After being dipped into the latex emulsion, the former is then heated to cure the polymer.

The elastomeric article of the present invention need not be formed from a coagulated latex emulsion. For example, in one embodiment, the elastomeric article of the present invention may be formed of a polymer which has been dissolved in a suitable solvent and then allowed to dry on a former in the desired shape as the solvent is evaporated from the solution. For example, one or more unsaturated block copolymers as are generally known in the art may be dissolved in a solvent, such as toluene, and may then be dried on a former in the shape of the desired elastomeric article. In one embodiment, styrene-isoprene-styrene (S-I-S) block copolymers, styrene-polybutadiene block copolymers (S-B), styrene-polybutadiene-styrene (S-B-S) block copolymers, and mixtures thereof can form the primary matrix of the glove. In one embodiment, the primary matrix of the glove can include a styrene-ethylene butylene-styrene (S-EB-S) block copolymer.

Various processing techniques as are generally known in the art may be incorporated into the present process. For example, an elastomeric layer may be gelled with heat to strengthen the elastomeric rubber film. If desired, the elastomeric layer may be leached with flowing hot water. A leaching process may extract various undesired constituents from the layer. This may cause the layer to shrink somewhat on the former and remove impurities. In one embodiment of the present invention, additional layers can be formed on the elastomeric base layer, such that the primary matrix of the glove includes multiple layers. Such a process is generally termed an over-dip process. In one embodiment, an over-dip process may be carried out by immersing the former including the base layer coating into an emulsion or a solution of a desired polymer. Additional layers on the primary matrix may, for instance, enhance certain characteristics of the glove. In one embodiment, the primary matrix of the glove may include an S-EB-S block copolymer layer and an over-dip layer of one or more other block copolymers, including, for example, S-I-S block copolymers, S-B block copolymers, and/or S-B-S block copolymers.

In accordance with the present invention, one or both surfaces of a glove's primary matrix may be at least partially coated with a crosslinked polymer layer. This may generally be achieved by immersing the former into an emulsion or a solution of the desired polymer before and/or after formation of the primary matrix. The polymer coating may, in one embodiment, for instance, form a donning coat on the skin contacting surface of the finished glove.

In one embodiment, in order to form a donning coat, the outside surface of the formed primary matrix on the former may be coated with the polymer composition. If desired, prior to immersing the former into the polymer composition, the surface of the formed primary matrix may be primed, such as with a dilute acid rinse followed by a water or aqueous alkali rinse. In an alternative embodiment, the polymer coating of the present invention may be formed on the former prior to formation of the primary matrix of the glove.

The polymer coating of the present invention, in one embodiment, includes a polymer or copolymer which includes negatively charged components. These components may provide reactivity with the desired cationic crosslinking agents. For example, polymers and copolymers which include pendant ester linkages to negatively charged terminal groups such as hydroxyl groups or amine groups, or include terminal carboxyl groups and the like may be used. In one embodiment, the polymer coating of the present invention may include a hydrogel polymer. In another embodiment, the polymer may be a vinyl addition polymer that can provide the desired negatively charged reactivity on pendant groups. In yet another embodiment, the reactive sites may be on the polymer backbone.

For exemplary purposes only, a non-limiting list of possible polymers which may be utilized in forming the polymeric coating of the present invention may include: polysaccharides including starches and cellulose such as carboxmethycellulose; polyacrylamides; polyacrylates such as polyacrylic acid, polymethacrylic acid, ethyl hexyl acrylate, hydroxyethyl methacrylate (HEMA), and the like; or polysiloxanes.

If desired, the polymeric coating of the present invention may include copolymers. For example, HEMA may be copolymerized with other polymers such as ethylhexyl acrylate or methacrylic acid to form the coating of the present invention. Other copolymers may be formed including, for example, silicones, acrylates, methacrylates, starches, polysaccharides, acrylamides and the like.

In general, in one embodiment, the former may be dipped or immersed into a solution including the desired polymer following formation of the primary matrix of the glove on the former. The former may be contacted with the polymer solution after dipping but prior to curing the elastomeric polymer forming the primary matrix of the glove. In other embodiments, the primary matrix may be cured first, prior to application of the polymer coating material of the present invention. In other embodiments, as described above, the polymer coating can be formed prior to formation of the primary matrix of the glove.

According to the present invention, the material forming the polymeric coating on a surface of the glove is crosslinked with a cationic crosslinking agent. In one embodiment, the crosslinking agent may be a polyamide epichlorohydrin crosslinking agent. Of particular advantage, PAE crosslinking agents are not formaldehyde-based. For example, a PAE crosslinking agent such as that sold under the Kymene® label by the Hercules Corporation of Wilmington, Del. may be a suitable cationic crosslinking agent. In one embodiment, Kymene®557LX may be used as a crosslinking agent.

In one embodiment, the former may be dipped or immersed into a single solution comprising both the desired polymer material and the crosslinking agent in forming the polymer coating. For example, the former may be dipped in a solution including both a HEMA polymer and a PAE crosslinking agent. The PAE crosslinking agent may be added to the polymer solution in an amount less than about 1% by weight of the solution. In one embodiment, a PAE crosslinking agent may be added to the solution in an amount less than about 0.5% by weight of the solution.

In certain embodiments, the PAE crosslinking agent may be diluted prior to addition to a polymer-containing solution. It has been shown that a polymer-containing solution of polyacrylic acid may be shocked if mixed with an undiluted PAE crosslinking agent. This may cause the acid to precipitate out of solution, thereby inhibiting formation of the polymer coating. This may occur at a wide range of solution pH, from about pH 2 to about pH 11. However, where the solution is formed from the sodium salt of polyacrylic acid, the PAE crosslinking agent may be added to the solution in undiluted form without causing precipitation.

In other embodiments, the glove may be contacted with the crosslinking agent in a separate process rather than contacted with a combined solution including both the polymer material and the crosslinking agent. For example, in one embodiment, after forming the primary matrix of the glove on the former, the former may be contacted with a solution including the crosslinking agent prior to contact with the polymer solution. Alternatively, the former may be contacted with the polymer solution prior to contact with the crosslinking agent solution.

In another embodiment, the crosslinking agent may be added to the solution or emulsion containing the elastomeric material used to form the primary matrix of the glove. For example, the crosslinking agent may be included in a base layer solution and/or an over-dip solution. In such embodiments, and depending upon the characteristics of the layer material and the solute, in addition to crosslinking the polymeric coating on the surface of the glove, the crosslinking agent may also crosslink the elastomeric polymer forming the primary matrix of the glove or a single layer of the primary matrix. For example, a natural or synthetic rubber latex coalesced on a former may be crosslinked by a PAE crosslinking agent which may be included in the latex emulsion dip.

The crosslinking agent may crosslink the polymer chains to form the polymeric coating of the present invention through covalent bonding, as at a terminal group. Alternatively, the chains may be crosslinked through ionic bonding, such as may occur at a negatively charged linkage on the polymer. In general, the cationic crosslinking agent may be attracted to and reactive with the negatively charged components on the polymer. In addition, the cationic crosslinking agent may also react with an elastomeric polymer in the primary matrix. For instance, the primary matrix may be formed from a single layer of a natural rubber latex. In this embodiment, the polyisoprene forming the primary matrix of the glove may include negatively charged reactive groups which may react with the crosslinking agent. Other rubber materials useful in forming gloves may also include negatively charged reactive groups which may react with the cationic crosslinking agent as well. For instance, certain block copolymers which may form a base layer or an over-dip layer of the primary matrix, for example, may also react with the cationic crosslinking agents.

In such embodiments, in addition to crosslinking the polymer forming the polymeric coating on a surface of the glove, the crosslinking agent may also crosslink the primary matrix material, and in addition, may form points of attachment between the adjacent layers of the glove. For example, in one embodiment, the polymeric coating of the present invention may be a donning coat, and the crosslinking agent may form crosslinks between the donning coat and the primary matrix which may help to prevent peeling and delamination of the polymeric coating of the present invention.

In those embodiments where the crosslinking agent reacts not only with the polymer forming the coating of the present invention, but also with the polymer(s) forming the primary matrix, the hydrophilic properties of the polymer coating may be controlled by varying the process conditions. For example, the number of hydrophilic reactive groups remaining unreacted in the cured polymer coating, which may affect the tactile characteristics of the glove, may depend not only on the amount of crosslinking agent added to the process, but also on how the crosslinking agent is added to the process. For instance, in certain embodiments, the crosslinking agent may be a component of the solution or emulsion including the elastomer that forms the primary matrix. In this embodiment, the crosslinking agent reacts primarily with the polymer forming the primary matrix and secondarily with the polymer of the coating layer, due to the proximity of the crosslinking agent to the elastomeric polymer. Thus, the crosslinking agent may primarily be contained in the primary matrix of the glove. As such, in this particular embodiment, the cured polymer coating may include a large number of unreacted hydrophilic sites and therefore exhibit greater hydrophilic properties than would be the case in a similar embodiment which differs only in that the crosslinking agent is combined in solution with the polymer coating material prior to contact with the primary matrix.

When contained in the coating solution or emulsion, in contrast, the crosslinking agent may be contained primarily in the polymeric coating of the glove and may be in closer proximity to the coating polymers than to the primary matrix polymers during the curing process. Thus, fewer unreacted hydrophilic groups may remain within the cured polymer coating, forming a polymeric coating with less hydrophilicity. In another embodiment, the crosslinking agent can be included in more than one of the dip-coating solutions which contact the nascent glove.

In addition, due to reactivity between PAE crosslinking agents and water, the moisture content of the layers may also affect the efficiency of the crosslinking process. PAE tends to hydrolyze in the presence of water. As such, the moisture content of the layer to be crosslinked in one embodiment may be relatively low, below about 6% by weight for example. In one embodiment, the moisture content of the uncured layer may be less than about 3% by weight in order to crosslink with a PAE crosslinking agent. In another embodiment, the moisture content of the layer may be less than about 1% by weight. In one embodiment, the layer may have a moisture content of about 0.6% by weight and may be crosslinked with a PAE crosslinking agent. As such, prior to crosslinking, the former which is carrying the uncured polymer material will be dried at a temperature below that at which substantial crosslinking may occur, for example at a temperature below about 100° C. in order to reduce moisture in the layers prior to crosslinking.

In one embodiment, when the layer to be crosslinked has a relatively high moisture content (above about 6%, for example), some of the crosslinking agent may react with the water, leaving less crosslinking agent available for crosslinking the polymer and, therefore, a more hydrophilic coating when cured. In contrast, under low moisture conditions, more crosslinking agent may be available for reaction with the polymer, and the polymer coating formed on the surface of the glove may have a higher degree of crosslinking and exhibit greater hydrophobicity.

For many applications, the polymeric coating on the glove should retain a degree of hydrophilic functionality so as to obtain the desired donning characteristics of the glove. Excessive absorbability of the polymer coating, however, may cause the layer to swell to the point of affecting the glove fit or causing the polymer coating to delaminate from the primary matrix of the glove and should therefore be avoided.

Figure 3:
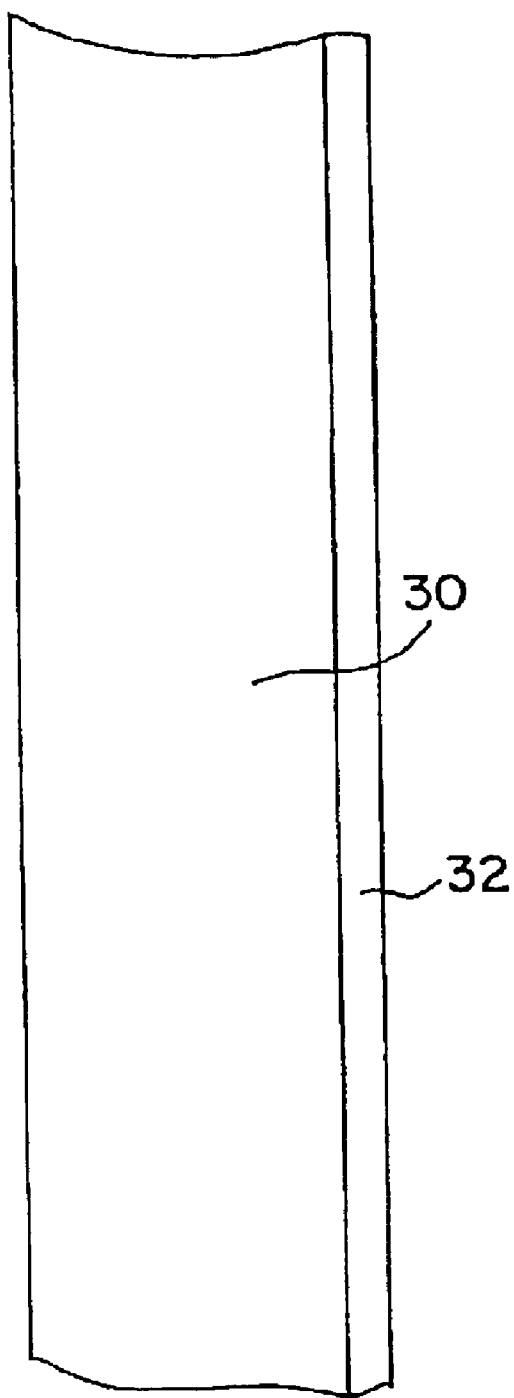
FIG. 3 is an enlarged cross-sectional view of one embodiment of an elastomeric article of the present invention.

FIG. 3 is an illustration of a cross section of a portion of one embodiment of an article made according to the present invention. In this particular embodiment, the primary matrix 30 of the glove is a single layer primary matrix. The polymeric coating 32 is applied to the surface of the primary matrix and crosslinked according to the present invention. The crosslinked polymer coating 32 on the surface of the primary matrix 34 can be a donning coating, and can improve the donning characteristics of the glove or can be a former release coating, preventing excessive adhesion between the primary matrix and the former. In one embodiment, the gloves of the present invention can include a polymeric coating formed according to the processes disclosed herein on both surfaces of the glove.

The amount of crosslinking agent to be used in forming the gloves of the present invention may vary widely depending upon process conditions and desired glove characteristics. For example, the amount of crosslinking agent added may depend upon whether the agent will crosslink the primary matrix in addition to the polymer coating, whether the agent will form crosslinks between the coating and the primary matrix, whether the crosslinking agent will be added in a separate dip solution or in conjunction with the coating polymer or the elastomeric polymer, and the desired level of hydrophilic functionality to be retained on the surface of the glove, among other possibilities. Generally, the ratio of coating polymer to crosslinking agent by weight used in the process may be between about 100:1 and about 1:10. For example, a PAE crosslinking agent may be used in an amount between about 1% and about 500% by weight of the polymer. In one embodiment, a PAE crosslinking agent may be added to the process in an amount between about 5% and about 50% by weight of the polymer. In one embodiment, the polymer and the PAE crosslinking agent may be in about a one to one ratio.

Curing time and degree of cure of the polymer coating may depend upon many factors, including concentration of the reactive constituents, pH, and temperature of the system. In general, crosslinking may occur at neutral to basic conditions. For instance, the emulsions and/or solutions containing the reactive constituents may generally be at a pH of between about 7 and about 11 for crosslinking to occur. In one embodiment, the compositions may be at a pH of between about 9 and about 11 for crosslinking to occur. In certain embodiments, pH adjustors may be added to the reactive constituents, in order to adjust the pH of the emulsions and/or solutions prior to crosslinking on the former.

In one embodiment, the polymer may be cured at a temperature of between about 100° C. and about 150° C. In one embodiment, the polymer may be cured and the rubber forming the main glove body may be vulcanized at the same time. In general, the latex is vulcanized by high temperature reaction with a vulcanizing agent to cause cross-linking of the polymer chains. As discussed above, in certain embodiments, the crosslinking agent of the present invention may serve to not only cure the outer polymer coating, but may also act as the vulcanizing agent. In other embodiments, the rubber may be vulcanized by a more standard vulcanizing agent, such as sulfur, while the crosslinking agent of the present invention may crosslink the outer coating and optionally form crosslinks between the outer coating and the primary matrix of the glove. It will be recognized by those skilled in the art that in certain embodiments, a vulcanization process will not be necessary in forming the elastomeric primary matrix of the glove.

In addition to vulcanizing the latex and/or curing the polymer coating, the high temperature process may cause the evaporation of any volatile components remaining on the former, including any remaining water. Therefore, the high temperature process may cause slight shrinkage in the glove. In general, the thickness of a glove wall formed by the processes of the present invention may be from about 3 mil to about 15 mil. In some embodiments, the thickness of a glove wall may be from about 3 mil to about 5.5 mil.

After the polymer coating is cured and the rubber forming the primary matrix is vulcanized (when necessary), other processes as are generally known in the art may be carried out. For example, after stripping, the gripping surface of the glove may be treated to improve gripping characteristics.

One or more water rinses of the glove following curing of the polymer coating of the present invention may remove any undesired compounds remaining on the surface of the glove. In one embodiment, the glove may be rinsed in a soft water rinse followed by a deionized water rinse to ensure limited bioburden on the gloves.

After rinsing, a lubricant may be applied to the glove to enhance damp donnability. For example, a silicone may be applied to the donning side of the glove. One such silicone is SM2140, a polydimethylsiloxane emulsion available from the General Electric Corporation. Examples of other suitable surfactant lubricants include cationic surfactants, such as hexadecyl trimethyl ammonium chloride and N-cetyl pyridinium chloride. Other suitable lubricants may include various fatty amine lubricants.

After any desired processing, the glove may be dried prior to packaging. For instance, the glove may be dried a first time for between about 30 minutes and about 60 minutes at 50° C. to 60° C., and then dried a final time for about 60 minutes at about 70° C. to 80° C.

The present invention may be better understood by reference to the following examples, which are provided by way of explanation of the invention, not as a limitation of the invention. In fact, it will be apparent to those skilled in the art that various modifications and variations may be made of this invention without departing from the scope or spirit of the invention.

EXAMPLE 1

A dispersion was prepared by mixing 250 g hot tap water and 5 g Methocel A4M (a methyl cellulose polymer available from the Dow Chemical Company). The solution was allowed to cool, with mixing, such that the Methocel dissolved.

2.1 g of 100% Kymene 557LX (a PAE crosslinking agent available from the Hercules corporation) was added to 100 g of the Methocel solution. The pH of this solution was adjusted to 9.0 with a potassium hydroxide solution.

A film of the solution was cast and dried/cured at 120° C. for 2 hours.

The resulting film would not dissolve in either hot or cold water. The insoluble film was measured to contain up to 97.4% water.

For comparison purposes, a similar mixture was prepared as above, however no PAE crosslinking agent was included in the mixture. The resulting film dissolved when contacted with water.

EXAMPLE 2

100 g of a polymer solution was prepared including 90 g of water and 10 g of polyacrylic acid, sodium salt (available from Polymer Science, Catalogue Number 06567). 100%

Kymene 557LX was then added to the solution and pH was adjusted in order to produce films, as follows:

| Film Number | Polymer Solution (g) | Kymene 557LX (g) | pH |
|---|---|---|---|
| 1 | 20 | 2 | 9.5 |
| 2 | 20 | 1 | 9.5 |
| 3 | 20 | 0.5 | 9.5 |
| 4 | 20 | 0 | 9.5 |
| 5 | 20 | 0 | about 7.3 (No adjustment) |

Films 1–5 were then cast and dried/cured under a heat gun for approximately 10 minutes. Films 1, 2, and 3 did not dissolve when contacted with water. Films 4 and 5 did dissolve when contacted with water.

As may be seen, a cationic crosslinking agent, such as a PAE crosslinking agent, may be used to crosslink a polymeric film to produce a hydrophilic, insoluble film which may be applied as a donning layer on an elastomeric article, such as a glove.

These and other modifications and variations to the present invention may be practiced by those of ordinary skill in the art, without departing from the spirit and scope of the present invention, which is more particularly set forth in the appended claims. Furthermore, those of ordinary skill in the art will appreciate that the foregoing description is by way of example only, and is not intended to limit the invention so further described in such appended claims.

What is claimed is:

1. An elastomeric article comprising:
   a primary matrix comprising an elastomeric polymer;
   a polymeric coating on a surface of the primary matrix, the polymeric coating comprising a coating polymer which is crosslinked with a polyamine epichlorohydrin crosslinking agent; and
   wherein the elastomeric article comprises a glove.
2. The elastomeric article of claim 1, wherein the coating polymer comprises a hydrogel polymer.
3. The elastomeric article of claim 1, wherein the coating polymer comprises hydroxyethyl methacrylate.
4. The elastomeric article of claim 1, wherein the coating polymer comprises a polyacrylate.
5. The elastomeric article of claim 1, wherein the coating polymer comprises a polysaccharide.
6. The elastomeric article of claim 5, wherein the coating polymer comprises carboxymethyl cellulose.
7. The elastomeric article of claim 1, wherein the coating polymer comprises a polyacrylamide.
8. The elastomeric article of claim 1, wherein the primary matrix comprises nitrile rubber.
9. The elastomeric article of claim 1, wherein the primary matrix comprises natural rubber.
10. The elastomeric article of claim 1, wherein the primary matrix comprises polyvinyl chloride.
11. The elastomeric article of claim 1, wherein the primary matrix comprises a block copolymer.
12. The elastomeric article of claim 11, wherein the block copolymer comprises a styrene-ethylene butylene-styrene block copolymer.
13. The elastomeric article of claim 1, wherein the primary matrix comprises more than one layer.
14. The elastomeric article of claim 13, wherein the polyamine epichlorohydrin crosslinking agent forms crosslinks between the layers of the primary matrix.
15. The elastomeric article of claim 1, wherein the polyamine epichlorohydrin crosslinking agent forms crosslinks between the polymeric coating and the primary matrix.
16. The elastomeric article of claim 1, wherein the polyamine epichlorohydrin crosslinking agent crosslinks the elastomeric polymer.
17. The elastomeric article of claim 1, wherein the polymeric coating is a donning coat.
18. The elastomeric article of claim 1, wherein the polymeric coating is a former release coat.
19. The elastomeric article of claim 1, further comprising a lubricant applied to the crosslinked polymer coating.
20. The elastomeric article of claim 19, wherein the lubricant is selected from the group consisting of a silicone lubricant, a surfactant lubricant, and a fatty amine lubricant.
21. An elastomeric glove comprising:
   a primary matrix comprising an elastomeric polymer, the primary matrix being in the shape of a glove defining an interior surface and an exterior surface; and
   a polymeric coating on a surface of the primary matrix, the polymeric coating comprising a coating polymer selected from the group consisting of polyacrylates, polyacrylamides, and polysaccharides, wherein the coating polymer is crosslinked with a polyamine epichlorohydrin crosslinking agent.
22. The elastomeric glove of claim 21, wherein the coating polymer comprises a hydrogel polymer.
23. The elastomeric glove of claim 21, wherein the coating polymer comprises hydroxyethyl methacrylate.
24. The elastomeric glove of claim 21, wherein the polymeric coating comprises carboxymethyl cellulose.
25. The elastomeric glove of claim 21, wherein the polymeric coating polymer is a copolymer.
26. The elastomeric glove of claim 21, wherein the primary matrix is formed from a natural or a synthetic latex.
27. The elastomeric glove of claim 21, wherein the primary matrix comprises a block copolymer.
28. The elastomeric glove of claim 27, wherein the block copolymer comprises a styrene-ethylene butylene-styrene block copolymer.
29. The elastomeric glove of claim 21, wherein the primary matrix comprises more than one layer.
30. The elastomeric glove of claim 21, wherein the polyamine epichlorohydrin crosslinking agent forms crosslinks between the polymeric coating and the primary matrix.
31. The elastomeric glove of claim 21, wherein the primary matrix comprises the elastomeric polymer crosslinked with the polyamine epichlorohydrin crosslinking agent.
32. The elastomeric glove of claim 21, wherein the polymeric coating is a donning coat.
33. The elastomeric glove of claim 21, wherein the crosslinking agent is contained primarily in the primary matrix.
34. The elastomeric glove of claim 21, wherein the crosslinking agent is contained primarily in the polymeric coating.
35. An elastomeric article comprising:
   a primary matrix comprising an elastomeric polymer; and
   a polymeric coating on a surface of the primary matrix, the polymeric coating comprising a coating polymer which is crosslinked with a polyamine epichlorohydrin crosslinking agent, the coating polymer comprising a hydrogel polymer or a polysaccharide.

36. An elastomeric article comprising:

a primary matrix comprising an elastomeric polymer;

a polymeric coating on a surface of the primary matrix, the polymeric coating comprising a coating polymer which is crosslinked with a polyamine epichlorohydrin crosslinking agent; and wherein the polyamine epichlorohydrin crosslinking agent crosslinks the elastomeric polymer.

37. An elastomeric article as defined in claim 36, wherein the polyamine epichlorohydrin crosslinking agent forms crosslinks between the polymeric coating and the primary matrix.

38. An elastomeric article comprising:

a primary matrix comprising an elastomeric polymer;

a polymeric coating on a surface of the primary matrix, the polymeric coating comprising a coating polymer which is crosslinked with a polyamine epichlorohydrin crosslinking agent; and wherein the elastomeric article comprises a condom.

* * * * *